(12) United States Patent
Bååt et al.

(10) Patent No.: US 9,883,841 B2
(45) Date of Patent: Feb. 6, 2018

(54) APPARATUS, SYSTEMS AND METHODS FOR PRODUCING X-RAY IMAGES

(71) Applicant: Solutions for Tomorrow AB, Väckelsång (SE)

(72) Inventors: Jan Bååt, Växjö (SE); Mattias Guldstrand, Väremds Nöbbele (SE); Martin Göran Yngvesson, Tävelsås (SE)

(73) Assignee: SOLUTIONS FOR TOMORROW AB (SE)

( * ) Notice: Subject to any disclaimer, the term of this patent is extended or adjusted under 35 U.S.C. 154(b) by 98 days.

(21) Appl. No.: 14/272,583

(22) Filed: May 8, 2014

(65) Prior Publication Data

US 2014/0241504 A1  Aug. 28, 2014
US 2017/0065237 A9  Mar. 9, 2017

Related U.S. Application Data

(63) Continuation of application No. PCT/SE2012/051259, filed on Nov. 14, 2012.
(Continued)

(30) Foreign Application Priority Data

Nov. 15, 2011 (SE) ..................................... 11510831
Nov. 15, 2011 (SE) ..................................... 11510849

(51) Int. Cl.
*A61B 6/00* (2006.01)

(52) U.S. Cl.
CPC .......... *A61B 6/4405* (2013.01); *A61B 6/4283* (2013.01); *A61B 6/4291* (2013.01);
(Continued)

(58) Field of Classification Search
CPC ... A61B 6/4405; A61B 6/4452; A61B 6/4458; A61B 6/545; A61B 6/547; A61B 6/587; A61B 6/588
See application file for complete search history.

(56) References Cited

U.S. PATENT DOCUMENTS 5,475,730 A * 12/1995 Galando ............. A61B 6/4405
378/157
7,581,884 B1   9/2009 Barnes et al.
(Continued)

FOREIGN PATENT DOCUMENTS

DE   102010023036 A1 * 12/2011
JP   4-164437        6/1992
(Continued)

OTHER PUBLICATIONS

PTO 15-103303 which is an English Translation of DE102010023036A1.*

*Primary Examiner* — Glen Kao
*Assistant Examiner* — Chih-Cheng Kao
(74) *Attorney, Agent, or Firm* — Condo Roccia Koptiw LLP

(57) ABSTRACT

A mobile X-ray apparatus for medical examination includes an apparatus for producing X-ray images having a digital Radiography detector positioned at a first spatial position, an X-ray tube assembly positionable at a second spatial position relative to the first spatial position, sensor(s) for providing the first spatial position and/or the second spatial position, a control unit for receiving the first and/or the second spatial position(s) from the at least one sensor and for controlling the first or second spatial position for alignment of the X-ray tube assembly with the detector based on the first and second spatial positions, a drive wheel, a base, optionally an elevating column, and a telescopic arm which is rotatable into a direction perpendicular to a driving
(Continued)

direction of the base. The apparatus is controllable to drive along a patient table and/or the X-ray tube assembly is height adjustable in front of a wall stand, for alignment.

14 Claims, 8 Drawing Sheets

Related U.S. Application Data

(60) Provisional application No. 61/560,314, filed on Nov. 16, 2011, provisional application No. 61/560,331, filed on Nov. 16, 2011.

(52) U.S. Cl.
CPC .......... *A61B 6/4452* (2013.01); *A61B 6/4458* (2013.01); *A61B 6/4482* (2013.01); *A61B 6/545* (2013.01); *A61B 6/547* (2013.01); *A61B 6/566* (2013.01); *A61B 6/587* (2013.01); *A61B 6/588* (2013.01); *A61B 6/4233* (2013.01); *A61B 6/548* (2013.01)

(56) References Cited

U.S. PATENT DOCUMENTS

| | | | |
|---|---|---|---|
| 7,881,435 | B2 | 2/2011 | Wu et al. |
| 2001/0044577 | A1* | 11/2001 | Braun .................. A61B 5/055 600/417 |
| 2003/0103597 | A1* | 6/2003 | Sklebitz ........................ 378/63 |
| 2004/0146142 | A1* | 7/2004 | Maijala ........................ 378/102 |
| 2005/0051447 | A1 | 3/2005 | Nakajo |
| 2006/0120512 | A1 | 6/2006 | Watanabe |
| 2007/0116182 | A1 | 5/2007 | Koren |
| 2008/0165931 | A1 | 7/2008 | Luusua |
| 2008/0240357 | A1 | 10/2008 | Jabri et al. |
| 2009/0207973 | A1 | 8/2009 | Yi |
| 2009/0310753 | A1* | 12/2009 | Halsmer et al. ............... 378/198 |
| 2011/0249805 | A1* | 10/2011 | Kralles et al. ................ 378/198 |
| 2012/0045037 | A1* | 2/2012 | Carmichael et al. ......... 378/198 |

FOREIGN PATENT DOCUMENTS

| | | | |
|---|---|---|---|
| JP | 200070244 | A | 3/2000 |
| JP | 200201914 | A | 7/2000 |
| JP | 2001224580 | A | 8/2001 |
| JP | 200201914 | A | 1/2002 |
| JP | 2002537049 | A | 11/2002 |
| JP | 2006296676 | A | 11/2006 |
| JP | 2009189790 | A | 8/2009 |
| JP | 2010115362 | A * | 5/2010 |
| JP | 2010220817 | A | 10/2010 |
| JP | 2011167296 | A | 9/2011 |
| WO | WO0049476 | | 8/2000 |

* cited by examiner

US 9,883,841 B2

APPARATUS, SYSTEMS AND METHODS FOR PRODUCING X-RAY IMAGES

CROSS-REFERENCE TO RELATED APPLICATIONS

This application is a continuation of Patent Cooperation Treaty Application No. PCT/SE2012/051259, filed Nov. 14, 2012, which claims the benefit of Swedish Patent Application No. 11510849, filed Nov. 15, 2011, Swedish Patent Application No. 11510831, filed Nov. 15, 2011, U.S. Provisional Patent Application No. 61/560,331, filed Nov. 16, 2011, and U.S. Provisional Patent Application No. 61/560,314, filed Nov. 16, 2011, the contents of which are hereby incorporated by reference herein.

FIELD

This disclosure pertains in general to the field of X-ray imaging. More particularly, the disclosure relates to a mobile X-ray apparatus for medical examination.

BACKGROUND

Various X-ray apparatuses are known. Some of the known X-ray apparatuses are stationary, and can not be moved. Others are mobile and can be moved. However, the prior art mobile X-ray apparatuses are bulky, heavy and large. They have batteries, which contain lead and acid. Thus, they are not environmentally friendly. Furthermore, for height adjustments of an X-ray tube, a counter balanced mechanism with a counter-weight is used, which further increases weight, and a tall vertical column, which blocks the view in front of the mobile X-ray apparatus for the steering person behind it during movement. In addition, the prior art mobile X-ray apparatuses are too large for convenient transportation.

Moreover, the prior art X-ray systems generally have many additional components, such as a maneuver console, a computer for examination of images, a fixed X-ray generator, various holders and a separate display unit, positioned at various places in an examination room.

Thus, it would be advantageous to reduce the number of components used for X-ray imaging.

In addition, many existing stationary X-ray systems use old analogue detectors.

Thus, it would be advantageous to provide means for upgrading systems with analogue detectors so that digital radiography detectors can be used, i.e. retrofitting.

From U.S. Pat. No. 8,021,045 B2, a portable X-ray apparatus is known. However, as can be seen in FIG. 1 of this document, the portable system is rather bulky and has a vertical column, which blocks the view in front of the mobile X-ray apparatus for the steering person behind it during movement.

Thus, there is a need for an improved mobile X-ray apparatus, which is compact, light and small.

An environmentally friendly mobile X-ray apparatus, having lead free and acid free batteries would also be advantageous.

It would also be advantageous to have a free view of what is in front of the mobile X-ray apparatus during driving or moving of the apparatus.

A mobile X-ray apparatus, which can easily be transported, would also be advantageous.

SUMMARY

Accordingly, embodiments of the present disclosure preferably seek to mitigate, alleviate or eliminate one or more deficiencies, disadvantages or issues in the art, such as the above-identified, singly or in any combination by providing an apparatus, a system and methods for producing X-ray images, according to the appended patent claims.

According to one aspect of the disclosure, an apparatus for producing X-ray images is provided. The apparatus comprises a digital radiography detector, positioned at a first spatial position. It also comprises an X-ray tube assembly positionable at a second spatial position at a distance relative the first spatial position. Furthermore, it also comprises at least one sensor for providing the first spatial position and/or the second spatial position. Sensors that can be used are angle sensors, compasses, inclinometers, gyros, potentiometers, encoders and/or GPS receivers. In addition, local GPS or local sensor networks can be used for an absolute positioning. These systems may include the use of magnets and/or triangulation. Moreover, the apparatus comprises a control unit for receiving the first spatial position and/or the second spatial position from the at least one sensor. The control unit is adapted to control the second spatial position or the first spatial position for alignment of the X-ray tube assembly with the digital radiography detector, based on the first and second spatial positions. Optionally the apparatus comprises a drive wheel, a base, a telescopic arm and/or an elevating column. The apparatus can be positioned quickly and easily.

According to another aspect of the disclosure, a system for producing X-ray images is provided. The system comprises a workstation, such as a patient table or a wall stand, and an apparatus. The control unit of the apparatus is configured to align the X-ray tube assembly with the workstation from data, provided by sensors, such as angle sensors, compasses, inclinometers, gyros, potentiometers, encoders and/or GPS receivers located at the workstation. The data used comprises identification data and position data. Optionally angle data of the workstation is included. With the provided data, embodiments simplify or facilitate the alignment of the X-ray tube assembly with the workstation.

According to yet another aspect of the disclosure, a system for producing X-ray images is provided. The system comprises a workstation, such as a wall stand or a patient table, and an apparatus, such as a mobile X-ray apparatus. The digital radiography detector of the apparatus is positioned at the workstation. The control unit of the apparatus is configured to control at least one actuator of the apparatus for aligning an X-ray tube assembly of the apparatus with the digital radiography detector based on the first and second spatial positions, i.e. the positions of the digital radiography detector and the mobile X-ray apparatus. Through the use of a tracking unit, automatic alignment of the X-ray tube assembly and the digital radiography detector is enabled. The alignment can be in a vertical plane and/or in a horizontal plane.

According to a further aspect of the disclosure, a method of producing X-ray images is provided. The method comprises positioning of a digital radiography detector at a first spatial position and positioning of a mobile X-ray apparatus at a second spatial position at a distance relative the first spatial position. The first spatial position and/or the second spatial position are received from at least one sensor. Furthermore, optionally adjustment of the height of an elevating column is performed. Adjustment of a rotational angle of a telescopic arm is optionally performed. In addition, as an option, adjustment of a length of the telescopic arm is performed. All the adjustments are based on the first and second spatial positions. Also tilting and/or rotating of an X-ray tube assembly to align the X-ray tube assembly with the digital radiography detector is performed, based on the first and second spatial positions, if needed. An X-ray image is obtained.

According to another aspect of the disclosure, a method of producing X-ray images is provided, which comprises positioning of a digital radiography detector at a first spatial position. Positioning of a mobile X-ray apparatus at a second spatial position at a distance relative the first spatial position is performed. The first spatial position and/or the second spatial position are received by a control unit from at least one sensor. Optionally, adjustment of the height of an elevating column is performed, based on the first and second spatial positions. Also adjustment of a rotational angle of a telescopic arm can optionally be performed, based on the first and second spatial positions. As an option, the length of the telescopic arm is also adjusted, based on the first and second spatial positions. If needed, tilting and/or rotating of an X-ray tube assembly to align the X-ray tube assembly with the digital radiography detector is performed, based on the first and second spatial positions. An X-ray image is obtained. Then, the digital radiography detector may be repositioned. Alternatively the mobile X-ray apparatus may be repositioned. Thereafter more X-ray images can be obtained. The repositioning of the digital radiography detector or repositioning of the mobile X-ray apparatus and the obtaining of X-ray images may continue until a desired number of X-ray images are obtained.

According to a further aspect of the disclosure, an apparatus for producing X-ray images is provided. The apparatus comprises a drive wheel and a base. The base comprises an elevating column, which is rotationally fixed in relation to the base. The base further comprises a control unit, which is adapted to control at least the drive wheel and the elevating column. The base also comprises a telescopic arm, which is rotatable around the elevating column and connected to the elevating column with a connecting element in a joint. The telescopic arm and the connecting element are located outside an outer segment of the elevating column. Thus, the telescopic arm and the connecting element can freely move outside an outer segment of the elevating column and therefore X-ray images can be obtained from a very low height, i.e. a height which is just above the bottom of the elevating column. The elevating column does not block the view in front of the driver, and the apparatus therefore provides for a safer driving or movement. The apparatus is also of a compact size, so that it can be transported easily. Thus, fast, easy and safe transportation of the mobile X-ray apparatus is provided.

According to another aspect of the disclosure, a system for producing X-ray images is provided. The system comprises a workstation and an apparatus. The control unit of the apparatus is configured to align the X-ray tube assembly with the workstation from data, provided by angle sensors, compasses, inclinometers, gyros, potentiometers, encoders and/or GPS receivers at the workstation. The data used comprises identification data and position data. Optionally angle data of the workstation is included. With the provided data, embodiments simplify or facilitate the alignment of the X-ray tube assembly with the workstation.

According to yet another aspect of the disclosure, a system for producing X-ray images is provided. The system comprises a workstation and an apparatus. The workstation comprises a movable digital radiography detector. The apparatus comprises a tracking unit for receiving spatial data of the digital radiography detector in relation to the apparatus from at least one sensor. Sensors that can be used are angle sensors, compasses, inclinometers, gyros, potentiometers, encoders and/or GPS receivers. In addition, local GPS or local sensor networks can be used for an absolute positioning. These systems may include the use of magnets and/or triangulation. The control unit of the apparatus is configured to control actuators of the apparatus for aligning an X-ray tube assembly of the apparatus with the digital radiography detector based on the spatial data. Through the use of a tracking unit, automatic alignment of the X-ray tube assembly and the digital radiography detector is enabled. The alignment can be in a vertical plane or in a horizontal plane.

According to a further aspect of the disclosure, a method of producing X-ray images is provided. The method comprises positioning of a mobile X-ray apparatus for use in medical examination. In the method, tracking of a movable digital radiography detector is performed. Furthermore, adjustment of the height of an elevating column is performed, if needed. If needed, adjustment of a rotational angle of a telescopic arm is performed. The telescopic arm and the connecting element are located outside an outer segment of the elevating column. Thus, the height of the telescopic arm can also be adjusted. In addition, adjustment of a length of the telescopic arm is performed, if needed. Also tilting and/or rotating of an X-ray tube assembly to align the X-ray tube assembly with the digital radiography detector is performed, if needed. An X-ray image is obtained.

According to another aspect of the disclosure, a method of producing X-ray images is provided, which comprises positioning of a mobile X-ray apparatus. Tracking of a movable digital radiography detector is performed. Adjustment of the height of an elevating column is performed, if needed. Also adjustment of a rotational angle of a telescopic arm is performed, if needed. The length of the telescopic arm is also adjusted, if needed. If needed, tilting and/or rotating of an X-ray tube assembly to align the X-ray tube assembly with the digital radiography detector is performed. An X-ray image is obtained. Then, the movable digital radiography detector may be moved and more X-ray images can be obtained. The movement of the digital radiography detector and the obtaining of X-ray images may continue until a desired number of X-ray images are obtained.

According to yet another aspect of the disclosure, a mobile X-ray apparatus is provided. The mobile X-ray apparatus comprises a base and a digital radiography detector. The digital radiography detector is insertable into the base of the mobile X-ray apparatus. The digital radiography detector is also storable in the slot.

According to a further aspect of the disclosure, a system for producing X-ray images is provided. The system comprises a workstation and a mobile X-ray apparatus. The mobile X-ray apparatus comprises a base and a digital radiography detector. The digital radiography detector is positionable at and/or attachable to a workstation. Furthermore, the digital radiography detector is also detachable from the workstation. Moreover, the digital radiography detector is insertable into a slot of the base of the mobile X-ray apparatus. In addition, the digital radiography detector is storable in the slot of the base of the mobile X-ray apparatus.

Further embodiments of the disclosure are defined in the dependent claims, wherein features for the second and subsequent aspects of the disclosure are as for the first aspect mutatis mutandis.

Some embodiments of the disclosure provide for enabling running cables or electrical wires inside the elevating column instead of outside the elevating column.

Some embodiments of the disclosure enable a compact size during transportation.

Some embodiments of the disclosure provide for fast and easy positioning of the apparatus.

Some embodiments of the disclosure provide for easy positioning and angling of the X-ray tube.

Some embodiments of the disclosure provide for easy maneuverability of the apparatus.

Some embodiments of the disclosure provide for convenient control of the apparatus.

Some embodiments of the disclosure provide for easy movement of the X-ray tube.

Some embodiments of the disclosure provide for easy adjustment of the height when transporting the device.

Some embodiments of the disclosure enable fast and easy imaging of different parts of a patient, since the apparatus can be automatically driven along a patient table for alignment of an X-ray tube assembly with a digital radiography sensor, based on tracking of the digital radiography sensor.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
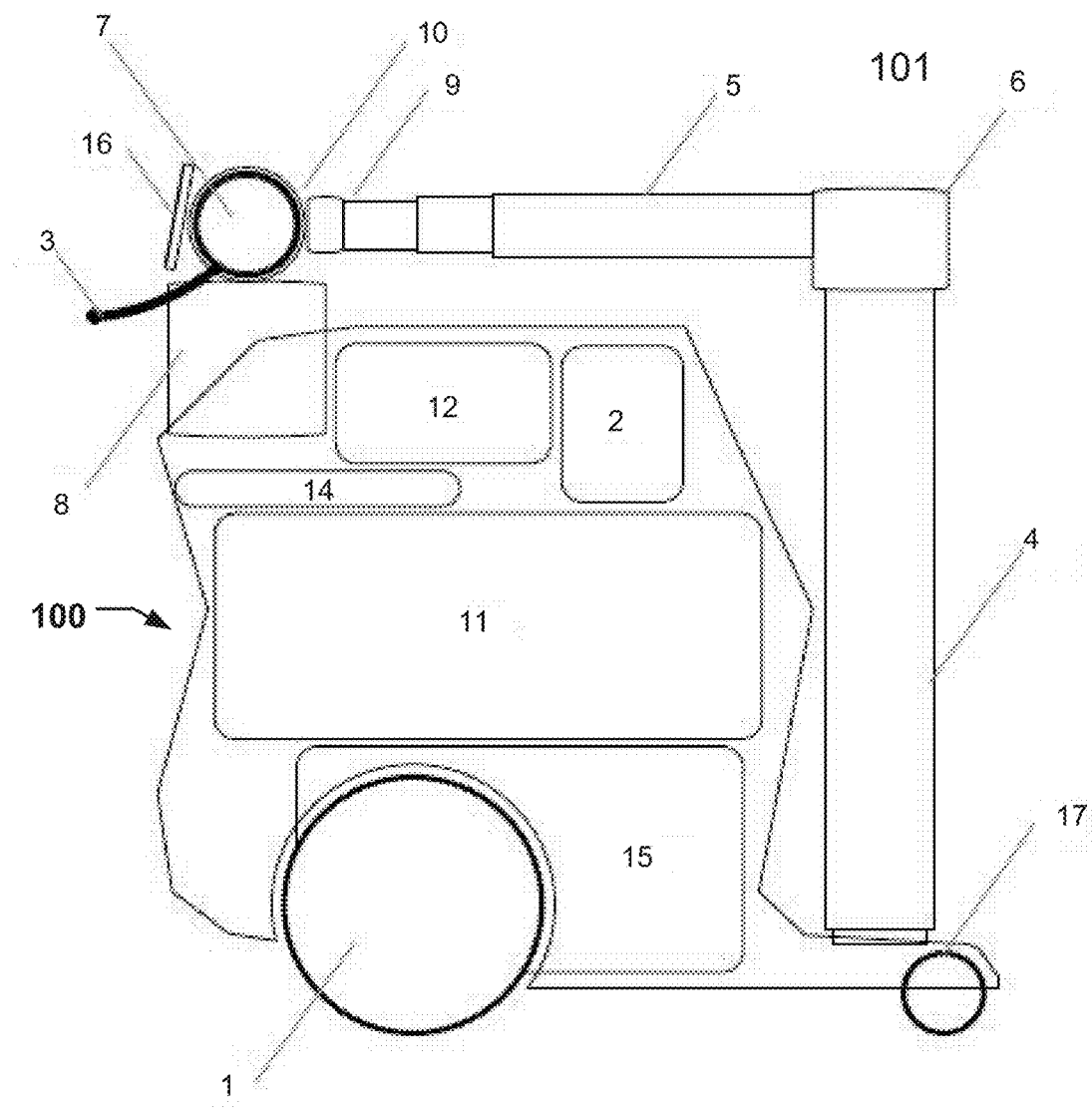
FIG. 1 is a lateral view of a mobile X-ray apparatus.

Reference will now be made in detail to the presently preferred embodiments of the invention, examples of which are illustrated in the accompanying drawings. Throughout the following detailed description, the same reference numerals refer to the same elements in all figures.

The following description focuses on an embodiment of the present disclosure applicable to an apparatus for producing X-ray images and in particular to a mobile X-ray apparatus. However, it will be appreciated that the disclosure is not limited to this application but may be applied to many other apparatuses for producing X-ray images, including for example stationary X-ray apparatuses.

In FIG. 1, which is a lateral view of a mobile X-ray apparatus 101, the core components of the mobile X-ray apparatus 101 can be seen. The mobile X-ray apparatus 101 comprises a base supported on two pairs of wheels, a front pair 17 and a back pair 1, and the back pair 1 is separately motorized and acting as drive wheels. Alternatively, the front pair is utilized as drive wheels. As another alternative, only one wheel is used as a drive wheel. Although, four wheels are described here, it should be understood that any other feasible number of wheels can be used. The drive wheels are controlled by a control unit 2, which receives user input from a user via the drive handle 3 during transportation. Also attached to the base 100 is a motorized column. The column may be an elevating column 4. The elevating column 4 is rotationally fixed in relation to the base. The elevating column 4 is controlled by a user via the drive handle 3 utilizing the control unit 2. Thus, the control unit 2 is adapted to control the elevating column 4 and/or the drive wheel. A rotatable telescopic arm 5 is attached to an outer column segment of the elevating column 4 in a joint by a connecting element 6, which is together with the telescopic arm 5 rotatable around the elevating column 5. Thus, the telescopic arm 5 is connected to the elevating column 4 with a connecting element 6 in a joint and rotatable around the elevating column 4. The telescopic arm 5 is balanced and can together with the connecting element be moved freely outside the outer segment of the elevating column 4. The connecting element is in one embodiment provided with an actuator, such as a motor, for rotational movement. This actuator is preferably a non-counterweight and/or non-balanced actuator. Thus, the base comprises an actuator, positioned outside the elevating column 4 for actuating a movement of the telescopic arm 5, and this actuator is preferably a non-counterweight and/or non-balanced actuator. The actuator is slidable outside the elevating column 4. At the end of the telescopic arm 5, an X-ray tube assembly is attached. The X-ray tube assembly comprises an X-ray tube 7 and a collimator 8. The X-ray tube assembly can be rotated 9 and tilted 10 around a centre axis of the telescopic arm 5. The X-ray tube assembly may be rotated 360 degrees. Optionally, the X-ray tube assembly movements and the collimator light field can be motorized. Since the telescopic arm 5 and the connecting element is located outside the outer segment of the elevating column 4 instead of inside the elevating column as in prior art, the space inside the elevating column 4 is available for other purposes, such as placement of electrical wires for the telescopic arm and the X-ray tube assembly. The energy transferred to the X-ray tube is generated by the built-in High Voltage generator 11.

The mobile X-ray apparatus 101 also comprises an Image system PC 12, a graphical control and image preview screen and a digital radiography detector slot or Flat Panel Detector (FPD) slot 14, i.e. a slot for storage of an FPD. This slot may also be used for other types of digital radiography detectors, such as High Density Line Scan Solid State detectors. The image system PC 12 is used for image processing. A preview of images is shown on the graphical screen. In addition or as an alternative, generator settings and/or system information is shown on the screen. Patient information, a booking list, different settings for examination, image settings and exposure settings can also be shown on the screen. In one embodiment, the screen is a touch screen, thus enabling both viewing and inputting of data. An FPD is wirelessly connected to the Image system PC. The batteries of the FPD are charged, when the FPD is positioned in the FPD slot. The FPD slot also protects the FPD during transportation. The entire apparatus is powered utilizing one or several built-in batteries 15. The batteries 15 are in one embodiment lead free and acid free. Thus, the batteries are environmentally friendly.

Figure 2:
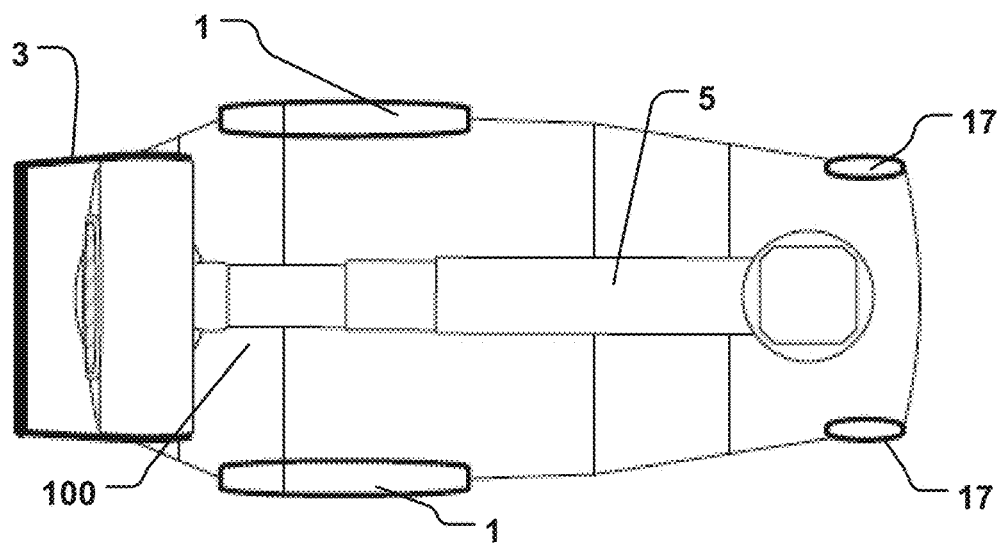
FIG. 2 is a top view of a mobile X-ray apparatus.

FIG. 2 is a top view of the mobile X-ray apparatus. In this figure, preferable positions of the wheels are depicted. Preferably, there is one pair of rear wheels 1 and one pair of front wheels 17. From FIG. 2, also the position of telescopic arm 5 during transportation can be seen. During transportation, the telescopic arm is placed in a transportation position on top of the mobile X-ray apparatus, i.e. the telescopic arm 5 is rotatably positionable into a position on top of the base 100 for transportation. This allows for a compact size of the mobile X-ray apparatus. In order to put the telescopic arm 5 into the transportation position, the telescopic arm 5 is either raised or lowered with the elevating column 4, dependent on where the telescopic arm is situated, so that the telescopic arm 5 is slightly above the top of the base 100. Thereafter, the telescopic arm is rotated into a position on top of the base 100. Then the telescopic arm 5 can be lowered, i.e. is lowerable into a locking position. Optionally, the telescopic arm 5 may also be locked in the locking position for safe transportation.

Figure 3A:
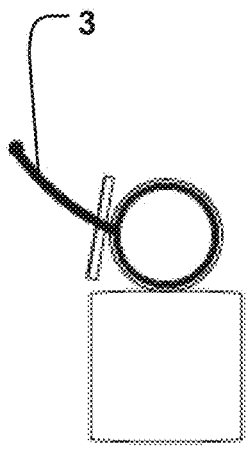
FIG. 3a is a lateral view of a drive handle in a park position.
Figure 3B:
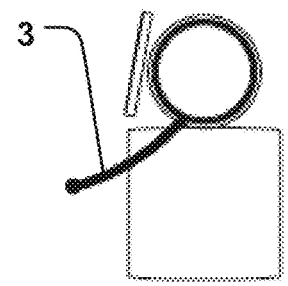
FIG. 3b is a lateral view of a drive handle in a drive position.

FIG. 3a is a lateral view of a drive handle 3 in a park position and FIG. 3b is a lateral view of a drive handle 3 in a drive position. Thus, these figures show the different positions of a drive handle 3. In FIG. 3a, the drive handle is in a drive position, and thus it is possible to move or drive the mobile X-ray apparatus. In FIG. 3b, the drive handle 3 has been lowered and is thus in a park position. When the drive handle 3 is in the park position, the mobile X-ray apparatus can not be transported or moved by a user. However, in one embodiment, it is still possible to automatically move the mobile X-ray apparatus, when the drive handle 3 is in the park position, such as along a patient table. It may also be possible to move the mobile X-ray apparatus slowly within a jog mode, even when the drive handle is in the park position. In one embodiment, the drive handle 3 is connected to and integrated with the X-ray tube 7 with strain gauges or strain gauge transducers, thereby facilitating easy movement of the X-ray tube 7 and/or movement of the apparatus, during transportation. The drive handle 3 may also be provided with a user interface unit, which is adapted to forward user inputs to the control unit 2. The X-ray tube 7 has an elongate shape and the drive handle 3 is integrally connected to the X-ray tube 7 at each end of the elongate X-ray tube 7. The height adjustment of the drive handle is located on the sides, i.e. at the ends of the elongate X-ray tube 7. The drive handle 3 can be used for controlling movement of the mobile X-ray apparatus, e.g. movement of the X-ray apparatus during transportation, as well as positioning of the X-ray tube assembly.

Figure 4:
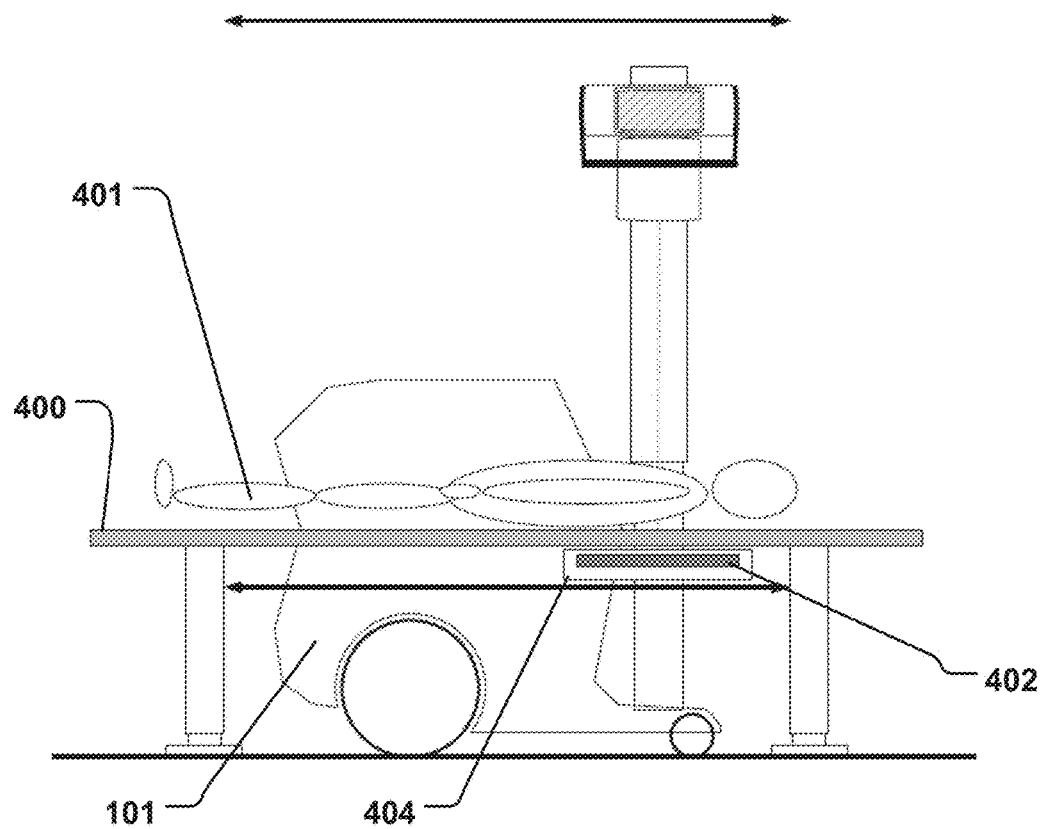
FIG. 4 is a lateral view of a patient table, with a mobile X-ray apparatus in the background.

In FIG. 4, a workstation can be seen. The workstation in this figure is a patient table 400. X-ray images of a patient 401 can be produced by the mobile X-ray apparatus 101. In one embodiment, a digital radiography detector 402 is moved manually or automatically between different positions along a patient table 400. The different positions of the digital radiography detector 402 correspond to different areas of a patient to be imaged. When the digital radiography detector is moved from one position to another position, the mobile X-ray apparatus tracks the movement and aligns the X-ray tube assembly with the digital radiography detector. This alignment may in one embodiment be achieved simply by the movement of the mobile X-ray apparatus in the direction of the wheels, i.e. the control unit 2 may control the drive wheels and move the mobile X-ray apparatus by driving the drive wheels until the mobile X-ray apparatus is aligned with the digital radiography detector. Thus, in this embodiment, the tracking is performed only in one horizontal direction. However, it should be understood that tracking can also be performed in more than one direction. Thus, in some embodiments, tracking is performed in three dimensions and movement of the mobile X-ray apparatus and/or X-ray tube assembly is performed in the three dimensions with appropriate actuators. Tracking is in some embodiments performed by the use of different sensors, such as angle sensors, compasses, inclinometers, gyros and/or GPS receivers. In some embodiments, there are sensors attached both to the X-ray tube assembly and to the digital radiography detector 402. The sensor signals from the digital radiography detector can be transmitted wirelessly to the control unit 2, either directly or via a tracking unit, located on the mobile X-ray apparatus. The tracking unit or the control unit 2 will receive spatial data, such as position data from the sensors. This spatial data may be data related to a first spatial position, e.g. a position of the digital radiography detector. The spatial data may as an alternative or in addition relate to a second spatial position, e.g. a position of the mobile X-ray apparatus. The data received by the tracking unit may further include identification data, position data, angle data and a checksum. If a separate tracking unit is used, then the control unit 2 receives data from the tracking unit. The control unit 2 of the apparatus is configured to control actuators of the apparatus for aligning an X-ray tube assembly of the apparatus with the digital radiography detector, based on the spatial data. Through the use of a tracking unit, automatic alignment of the X-ray tube assembly and the digital radiography detector is enabled. As an alternative, the tracking unit may be part of the control unit 2. Preferably, the sensors used for the digital radiography detector 402 utilize a Snap-On holder, so that they can be easily attached and detached from the digital radiography sensor.

Figure 5:
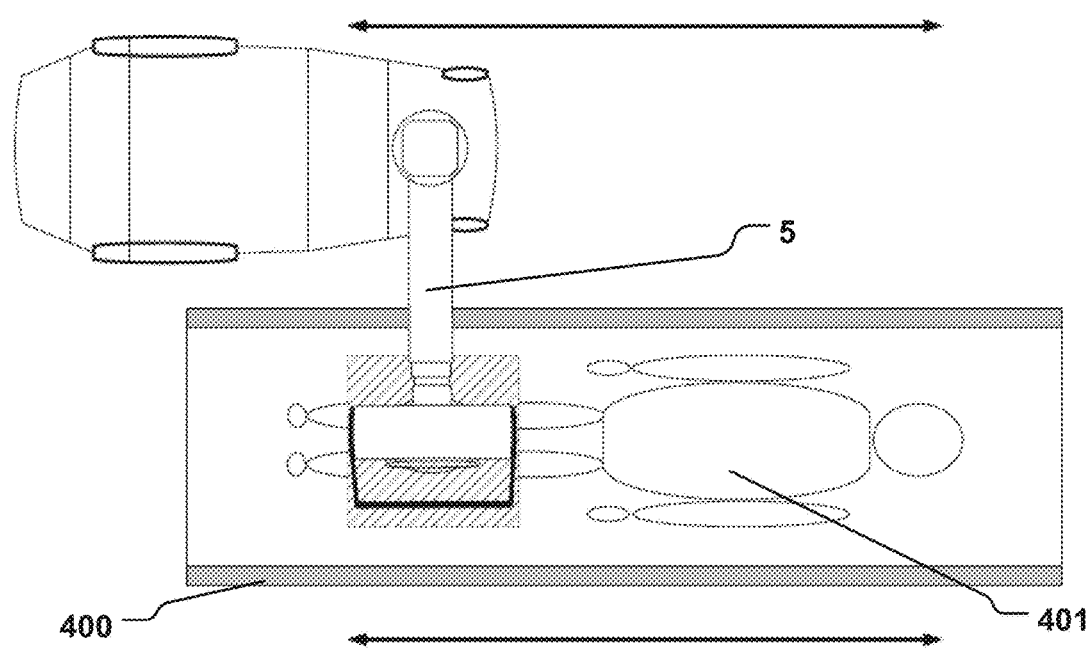
FIG. 5 is a top view of a patient table and a mobile X-ray apparatus.

FIG. 5 is a top view of a patient table 400 and a mobile X-ray apparatus. From FIG. 5, it can be seen that the telescopic arm 5 of the mobile X-ray apparatus has been turned, so that it is perpendicular to the patient table 400. The mobile X-ray apparatus is positioned in parallel with the patient table 400. Thus, the mobile X-ray apparatus can be driven along the patient table 400, if more than one area of the patient 401 needs to be imaged. In one embodiment, the mobile X-ray apparatus is driven along the patient table 400 according to tracks, such as magnetic tracks, on the floor. In this embodiment, the control unit 2 may control movement of the mobile X-ray apparatus in accordance with position data retrieved from the magnetic tracks. The position data may be accompanied with ID data and/or a checksum. The control unit 2 may also compare the position data from the magnetic track with position data received from the digital radiography detector 402, and based on this comparison align the X-ray tube assembly with the digital radiography detector 402. The tracks used may instead of magnetic tracks be mechanical tracks or rails. The tracks do not need to be on the floor. Instead, the tracks can be in the ceiling, on the wall or on a table, such as a patient table. If mechanical rails are used, then position data may be transmitted to the control unit 2 from position sensors, such as potentiometers or encoders, via an electrical wire or wirelessly. As an alternative of using tracks, optical marks or indications may instead be followed by the mobile X-ray apparatus. In another embodiment, the mobile X-ray apparatus may be guided in its movement by a mechanical arm attached to the workstation or in proximity to the workstation. In this embodiment, there is no need for retrieval of position data, since the position of the mobile X-ray apparatus is known, i.e. predetermined.

Figure 6:
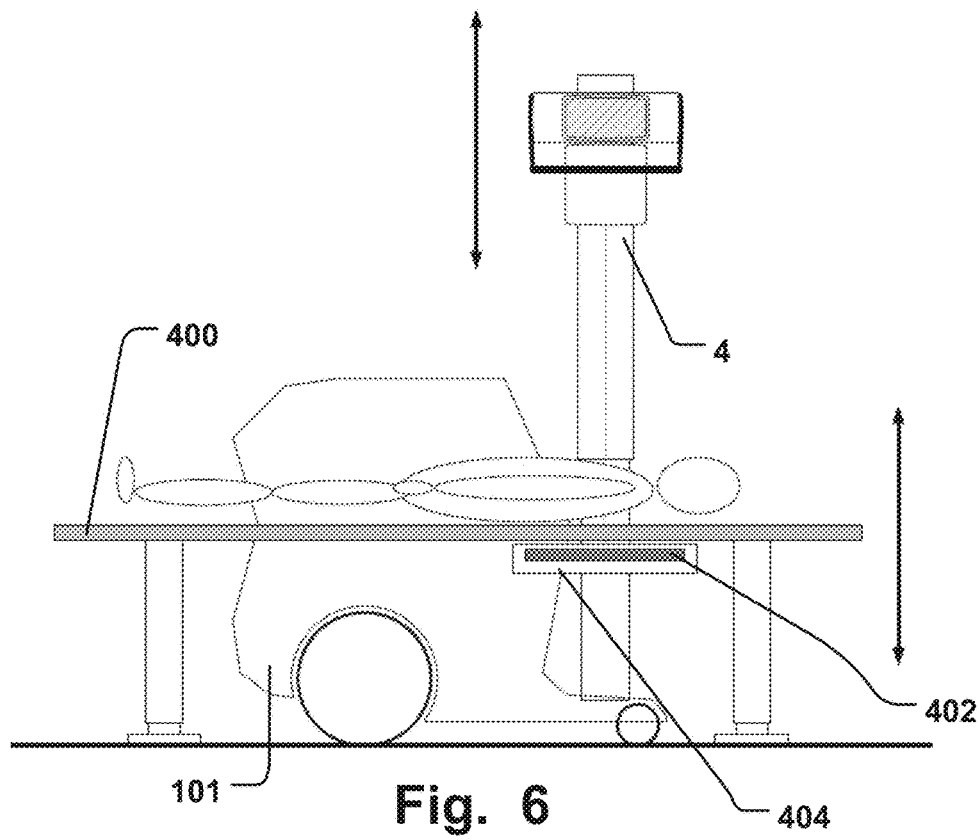
FIG. 6 is a lateral view of a patient table, with a mobile X-ray apparatus in the background.

In an embodiment according to FIG. 6, the tracking of the digital radiography detector 402 is instead performed in a vertical direction. Once the digital radiography detector 402 has been tracked, the X-ray tube assembly will be positioned at an appropriate distance from the digital radiography detector 402 by adjusting the height of the X-ray tube assembly with the elevating column 4.

Figure 7:
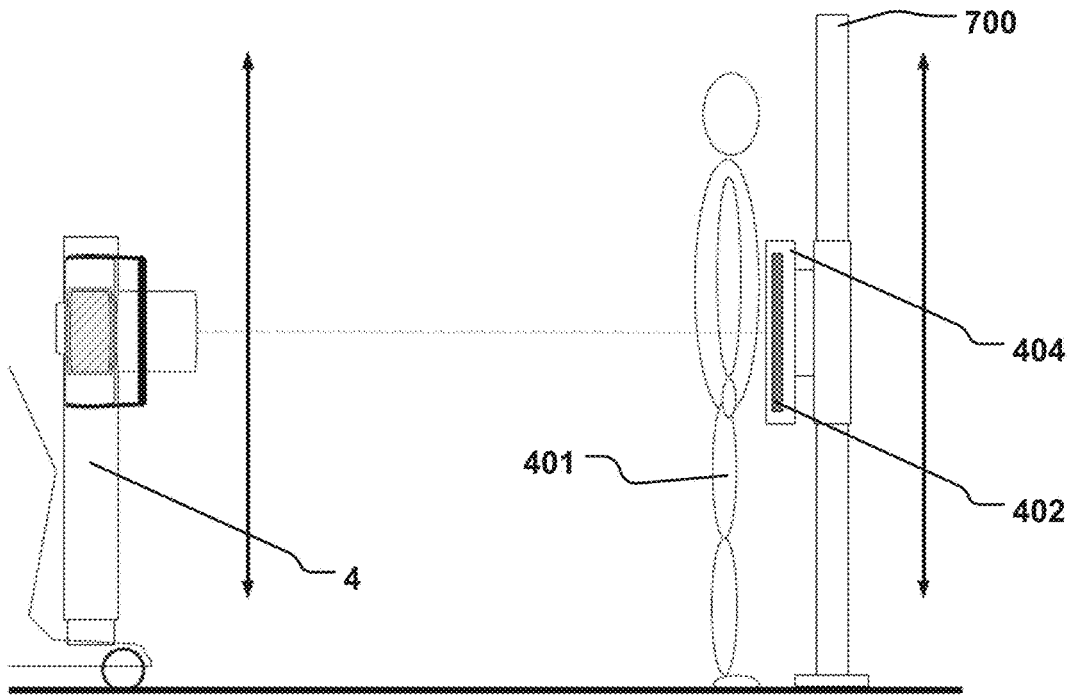
FIG. 7 is a lateral view of a workstation and a mobile X-ray apparatus.

FIG. 7 shows another embodiment, in which the elevating column 4 adjusts the height of the X-ray tube assembly in order to align it with the digital radiography detector 402. In this embodiment, the digital radiography detector 402 is placed in a holder 404 of another type of workstation, i.e. a wall stand 700. In this embodiment, the holder 404 with the digital radiography detector 402 can be moved into different positions at different heights depending on which part of the patient 401 is to be imaged. In one embodiment, an actuator, such as a motor, is used for moving the holder 404 into different positions automatically. This actuator can be controlled wirelessly, via wireless transceivers, from the control unit 2.

Figure 8:
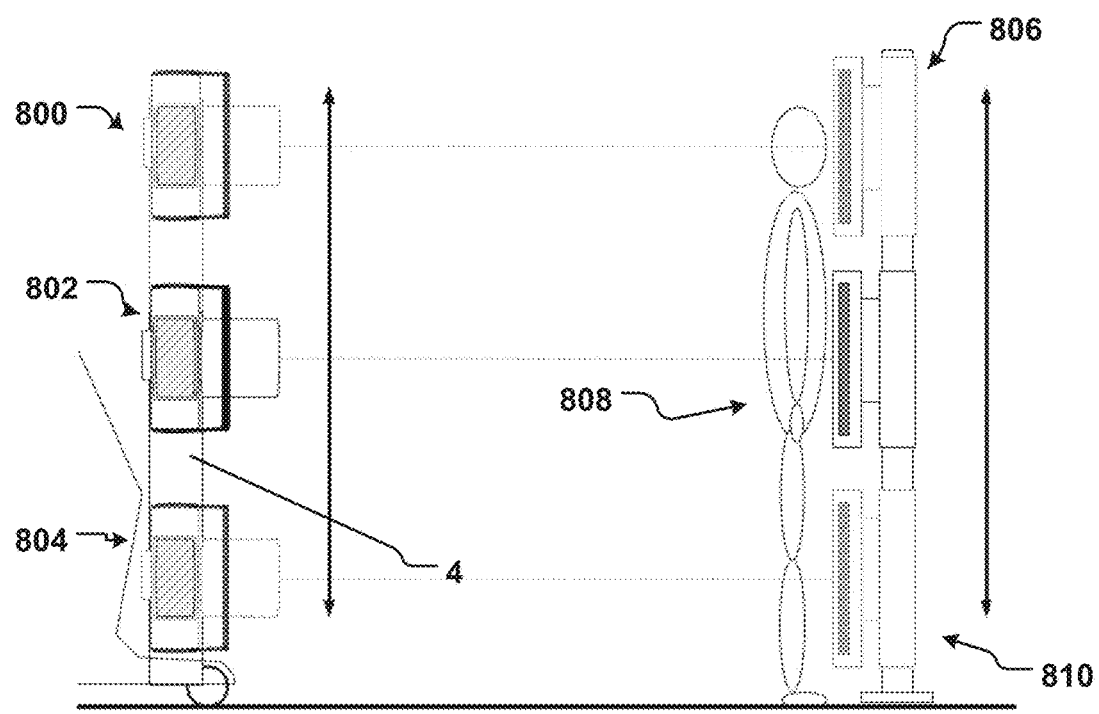
FIG. 8 is a lateral view of a wall stand and a mobile X-ray apparatus.

FIG. 8 shows different positions of the X-ray tube assembly. The X-ray tube assembly is put into the positions 800, 802 and 804 by moving the elevating column 4 as a response to a tracking action, which action tracks the digital radiography sensor 402 to one of the positions 806, 808, 810. In one embodiment, the actual holder 404 is tracked instead of the digital radiography detector 402. Thus, in this embodiment the sensors for tracking are located in or in proximity to the holder 404 and the sensor signals are transmitted wirelessly to the control unit 2.

Figure 9:
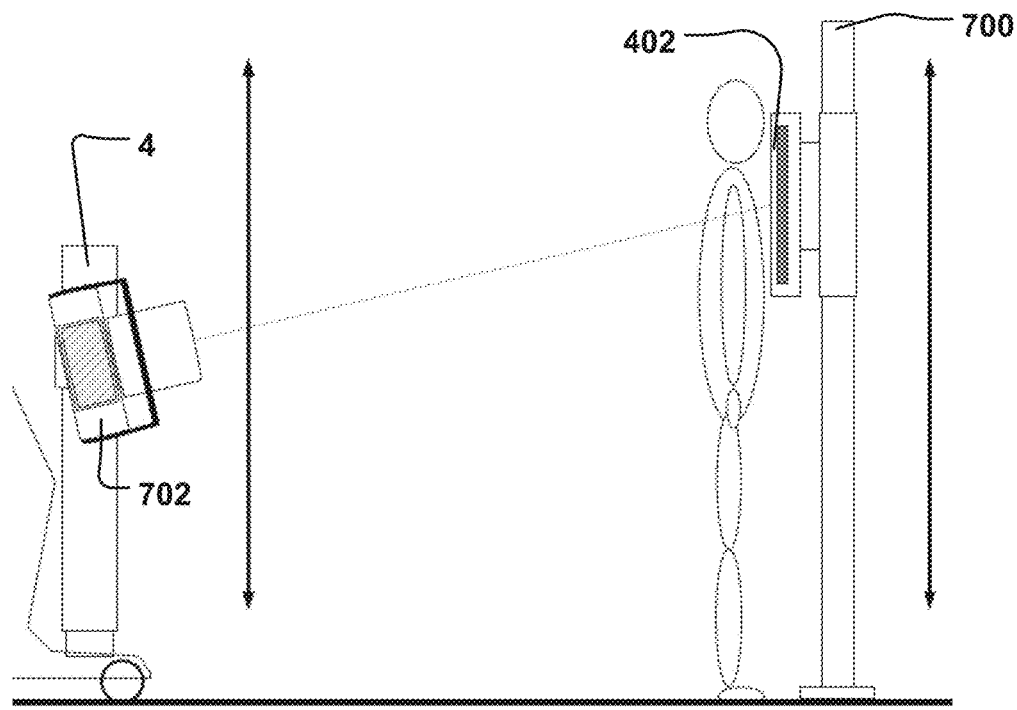
FIG. 9 is a lateral view of a wall stand and a mobile X-ray apparatus, with an X-ray tube assembly angled.

FIG. 9 is a lateral view of a wall stand 700 and a mobile X-ray apparatus, with an X-ray tube assembly 702 angled. In this figure, the X-ray tube assembly 702 is angled. In one embodiment, the X-ray tube assembly 702 is first angled to an appropriate angle manually or automatically. Then, the digital radiography detector 402 is tracked and the X-ray tube assembly 702 lifted to the appropriate height by the elevating column 4, based on the angle of the X-ray tube assembly 702 in relation to the elevating column 4. If needed, the angle can be measured with e.g. an angle sensor or an inclinometer. The height adjustment of the X-ray tube assembly 702 can instead or in addition be based on the distance between the digital radiography detector 402 and the mobile X-ray apparatus. This distance can be calculated from position data received from magnetic tracks and from the digital radiography detector 402. Alternatively, if mechanical rails are used, then position data may be transmitted to the control unit 2 from position sensors, such as potentiometers or encoders, via an electrical wire or wirelessly. As another alternative, the distance can be given from the optical marks, e.g. a predetermined distance is given at a certain optical mark. The angled X-ray tube can also be utilized for tomography images, tomosynthesis, stitching of images into panorama images or automatic tracking of workstations and digital radiography detectors. Tracking can for instance be performed as pendulum tracking.

Figure 10A:
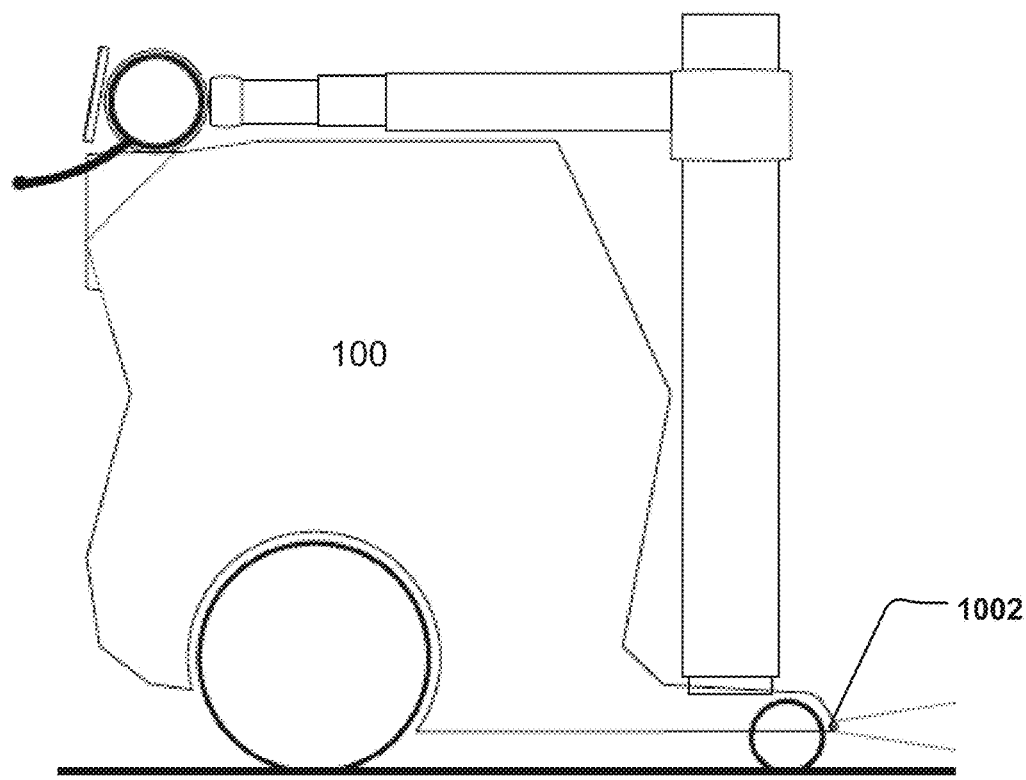
FIG. 10a is a lateral view of a mobile X-ray apparatus, with proximity sensors.

FIG. 10a is a lateral view of a mobile X-ray apparatus, with proximity sensors. As can be seen in this figure, a proximity sensor 1002 is positioned at the front of the mobile X-ray apparatus' base 100. The proximity sensor 1002 is able to detect the presence of nearby objects without any physical contact. When a proximity sensor 1002 senses an object, which intercepts the travelling path of the mobile X-ray apparatus, the user may be warned, so that he or she can stop the movement of the mobile X-ray apparatus. As an alternative, the mobile X-ray apparatus may be stopped automatically when a proximity sensor 1002 detects an object in front of the mobile X-ray apparatus.

Figure 10B:
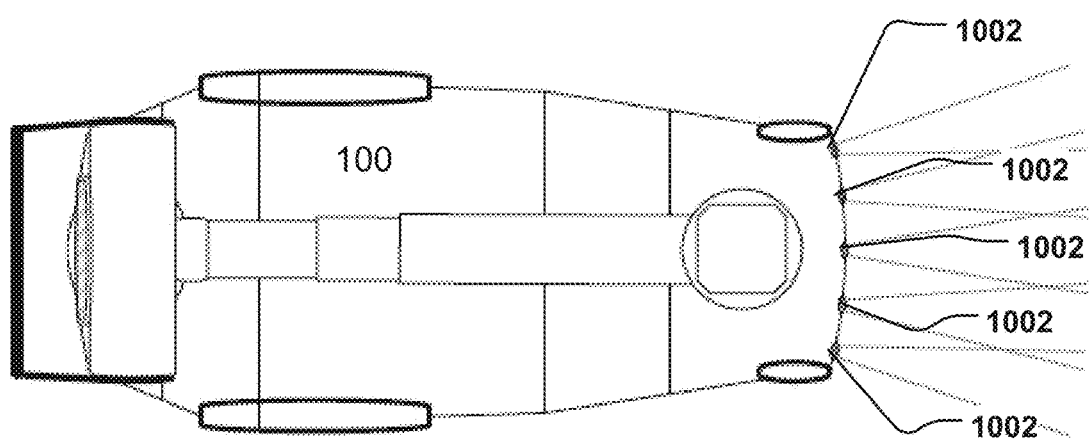
FIG. 10b is a top view of a mobile X-ray apparatus, with proximity sensors.

In FIG. 10b, several proximity sensors 1002 are shown. These proximity sensors 1002 are positioned all along the front of the base 100, each proximity sensor 1002 with a short distance to the next proximity sensor 1002. Although there are five proximity sensors 1002 displayed in the figure, it should be understood that any feasible number of proximity sensors can be used.

Figure 11A:
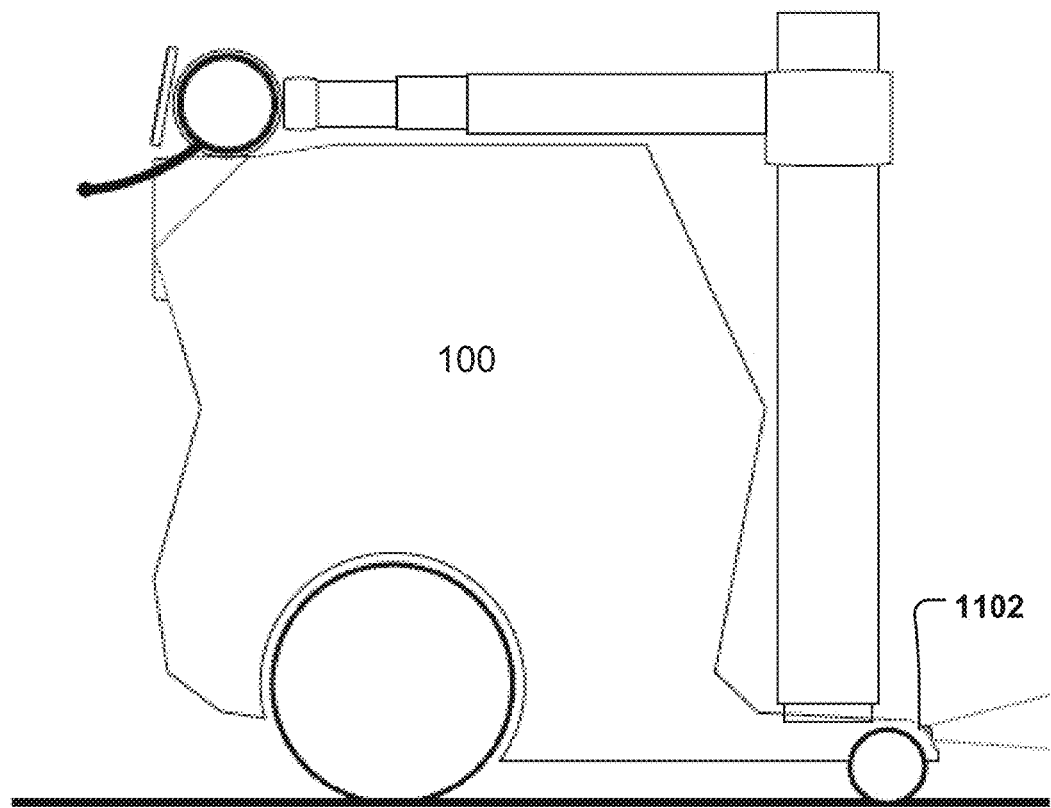
FIG. 11a is a lateral view of a mobile X-ray apparatus, with an integrated camera for forward view.
Figure 11B:
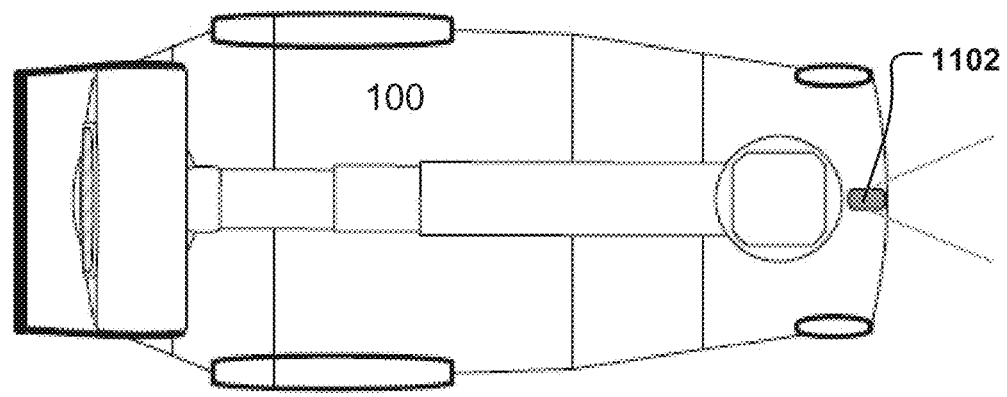
FIG. 11b is a top view of a mobile X-ray apparatus, with an integrated camera for forward view.

In another embodiment depicted in FIG. 11a and FIG. 11b, a camera or a video camera 1102 is mounted on the front part of the base 100. The images from the video camera 1102 are sent to the screen, so that the user can see what is in front of the mobile X-ray apparatus during transportation of the mobile X-ray apparatus. In one embodiment, the mobile X-ray apparatus is equipped with both proximity sensors 1002 and at least one camera 1102. By the use of a camera and/or proximity sensors, the mobile X-ray apparatus can be safely moved and/or transported.

Figures 12A, 12B, 12C:
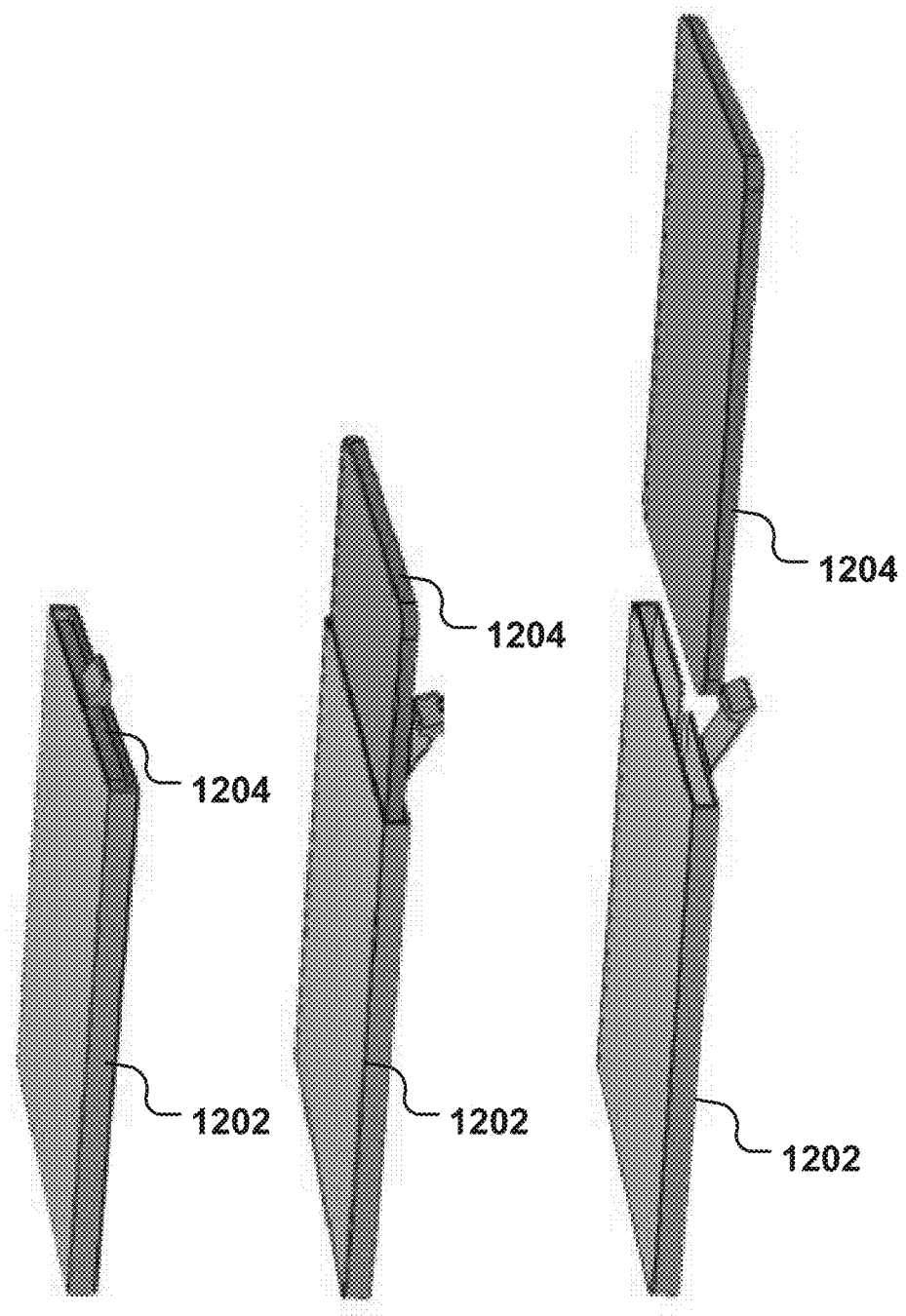
FIG. 12a is a view of a digital radiography detector with a grid unit mounted thereon.
FIG. 12b is a view of a digital radiography detector being partly inside a grid unit.
FIG. 12c is a view of a digital radiography detector and a grid unit.

In some embodiments, depicted in FIGS. 12a-c, the mobile X-ray apparatus 101 comprises a digital radiography detector slot 14 (shown schematically in FIG. 1). The digital radiography detector slot 14 may be utilized for storage of an image receptor 1204, such as a digital radiography detector 402 or an analog cassette. In many radiologic examinations a grid unit 1202 is used for suppression of noise, caused by scattered X-rays, in images. The grid unit 1202 is basically in the form of a thin cover, which may surround the image receptor 1204, i.e. the image receptor 1204 may be put inside the grid unit 1202. Thus, it is also possible to store the grid unit 1202 with or without the image receptor 1204 inside the digital radiography detector slot 14, e.g. when the grid unit 1202 and/or the image receptor 1204 are not being used. If both the image receptor 1204 and the grid unit 1202 are stored in the slot 14, a user may select whether to eject the image receptor 1204 with or without the grid unit 1202 mounted thereon.

Loading of the image receptor 1204 into the slot 14 when the grid unit 1202 is inside the base unit 100 may be performed by inserting the image receptor 1204 slightly angled. This way, good ergonomics is provided for the user, since the angled insertion of the image receptor 1204 reduces the muscular tension in the arms of the user. The angled insertion also makes the loading of the image receptor 1204 simpler due to gravitational force. Furthermore, the height of the slot 14 from the floor may also be selected so that good ergonomics is provided for the user. As an example, the slot opening may be located 50-150 cm, and preferably 60-80 cm, above the floor level.

Once the image receptor 1204 has entered through the slot opening, the image receptor 1204 should slide down to the bottom of the slot 14. When the image receptor 1204 reaches the bottom of the slot 14, the image receptor 1204 will be locked inside. The locking mechanism may be a mechanical spring mechanism or similar.

Loading of the image receptor 1204 with the grid unit 1202 mounted thereon is performed in the same way as loading of the image receptor 1204 into the slot 14 when the grid unit 1202 is inside the base unit 100.

Unloading of the image receptor 1204 may be performed by a user simply by activating eject. Eject may be activated by pushing on the visible side of the image receptor 1204. When eject is activated, the image receptor 1204 is automatically pushed outwards 2-30 cm, and preferably 10-15 cm. This pushing may be performed by e.g. a mechanical spring mechanism. When the image receptor 1204 is in this ejected position, a plastic protection bag can easily be mounted on top and/or around the image receptor 1204 if needed for examination. A plastic protection bag is typically used for applications, in which the image receptor 1204 may otherwise get in contact with fluids. Furthermore, while the image receptor 1204 is in the ejected position, the user may grip the image receptor 1204 with a safe two-hand-grip and pull the image receptor 1204 out, while the grid unit 1202 stays inside the base unit 100. Thus, good ergonomics is provided for the user also during unloading of the image receptor 1204.

Alternatively, the image receptor 1204 may be unloaded from the base unit 100 with the grid unit 1202 mounted thereon. When the grid unit 1202 is inside the base unit 100 and the image receptor 1204 is outside the base unit 100, the user may load the image receptor 1204 into the base unit 100 and into the grid unit 1202. This may be performed by the user through activation of the grid selection device, which preferably is mechanical. Thereafter, the user activates eject by pushing on the visible side of the image receptor 1204. When eject is activated, the image receptor 1204 is automatically pushed outwards 10-15 cm. This pushing may be performed by e.g. a mechanical spring mechanism. When the image receptor 1204 is in this ejected position, a plastic protection bag can easily be mounted on top and/or around the grid unit 1202 containing the image receptor 1204 if needed for examination. Furthermore, while the grid unit 1202 containing the image receptor 1204 is in the ejected position, the user may grip the grid unit 1202 with a safe two-hand-grip and pull the grid unit 1202 with the image receptor 1204 out from the base unit 100. Thus, good ergonomics is provided for the user also during unloading of the grid unit 1202 containing the image receptor 1204.

As an alternative, the grid unit 1202 may instead be mounted and dismounted by the user outside the slot 14.

Compared to a prior art X-ray systems, the disclosed mobile X-ray apparatus comprises fewer components. As an example, the disclosed X-ray apparatus does not need any additional maneuver console, any additional computer for examination of images, any fixed X-ray generator, any separate display unit or the holders usually used in a prior art X-ray system. Thus, a simpler and more cost-effective X-ray system is provided. Furthermore, the novel mobile X-ray system may be utilized as a fixed system, and thus replace a fixed X-ray system, although still being mobile.

Furthermore, with the disclosed mobile X-ray apparatus, systems with analogue detectors can easily be upgraded to use digital radiography detectors, since the only additional component needed to upgrade such a system is the mobile X-ray apparatus.

The present disclosure has been described above with reference to specific embodiments. However, other embodiments than the above described are equally possible within the scope of the disclosure. Different method steps than those described above, may be provided within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An apparatus for producing X-ray images, comprising:
at least one drive wheel; and
a base, comprising:
    an elevating column, rotationally fixed to said base;
    a control unit, adapted to control at least said at least one drive wheel and said elevating column;
    a telescopic arm, said telescopic arm is connected to said elevating column with a connecting element in a joint, and said telescopic arm and said connecting element being rotatable around said elevating column; and
    wherein said telescopic arm and said connecting element are located radially outside an outer segment of said elevating column allowing for free movement of said telescopic arm and said connecting element outside said outer segment of said elevating column.

2. The apparatus according to claim 1, wherein said base further comprises an actuator, positioned outside said elevating column for actuating a movement of said telescopic arm.

3. The apparatus according to claim 2, wherein said connecting element comprises said actuator, which is slidable around said elevating column.

4. The apparatus according to claim 2, wherein said actuator comprises at least one of a non-counterweight or a non-balanced actuator.

5. The apparatus according to claim 1, wherein said telescopic arm is rotatably positionable into a position on top of said base for transportation; and wherein said telescopic arm is arranged to first be rotated into a position on top of said base, and wherein said telescopic arm is lowerable into a locking position for locking in said locking position for safe transportation.

6. The apparatus according to claim 1, further comprising an X-ray tube assembly adapted for rotating and tilting motion around a center axis of said telescopic arm or an axis in parallel with said center axis of said telescopic arm and wherein said rotating and tilting motion is actuateable by a motor.

7. The apparatus according to claim 1, wherein said base further comprises a drive handle comprising a user interface unit adapted to forward user inputs to said control unit.

8. The apparatus according to claim 7, wherein said drive handle is connected to and integrated with an X-ray tube.

9. The apparatus according to claim 8, wherein strain gauge transducers are arranged in a connection between said drive handle and said X-ray tube, thereby providing a signal for feedback movement of said X-ray tube and/or movement of said apparatus, during transportation; and/or wherein said X-ray tube has an elongate shape and wherein height adjustment of said drive handle is located at each end of said elongate X-ray tube.

10. The apparatus according to claim 1, wherein said control unit is configured to control movement of said apparatus in accordance with position information retrieved from a track unit at a floor, wall or ceiling adjacent said apparatus.

11. The apparatus according to claim 1, wherein said telescopic arm is rotatable into a direction perpendicular to a driving direction of said base.

12. The apparatus according to claim 1, further comprising a digital radiography detector, said digital radiography detector being positionable at a workstation and storable in a slot of said base.

13. The apparatus of claim 12, wherein said digital radiography detector is storable inside a detachable grid unit in said slot of said base.

14. The apparatus of claim 13, wherein said digital radiography detector and said grid unit are stored in said slot and wherein a user can select said digital radiography detector to be ejected with or without said grid unit mounted thereon.

* * * * *